United States Patent [19]

Evans et al.

[11] 4,446,113
[45] May 1, 1984

[54] BENZOPYRANS

[75] Inventors: John M. Evans, Roydon; Robin E. Buckingham, Welwyn Garden; Kenneth Willcocks, Harlow, all of England

[73] Assignee: Beecham Group p.l.c., England

[21] Appl. No.: 423,450

[22] Filed: Sep. 24, 1982

[30] Foreign Application Priority Data

Sep. 25, 1981 [GB] United Kingdom ............... 8129064
Mar. 4, 1982 [GB] United Kingdom ............... 8206400
Apr. 8, 1982 [GB] United Kingdom ............... 8210490

[51] Int. Cl.³ .................... A61K 31/35; A61K 31/33; C07D 405/04; C07D 311/68
[52] U.S. Cl. .................... 422/267; 424/274; 424/278; 546/16; 546/196; 548/407; 548/525; 549/345; 549/399
[58] Field of Search ............... 546/196, 15; 548/525, 548/407; 424/267, 274, 278; 549/399, 345

[56] References Cited

U.S. PATENT DOCUMENTS 4,366,163 12/1982 Evans et al. .................... 546/196

FOREIGN PATENT DOCUMENTS 9912 4/1980 United Kingdom ............... 546/196

Primary Examiner—Robert T. Bond
Attorney, Agent, or Firm—Jacobs & Jacobs

[57] ABSTRACT

Compounds of formula (I):

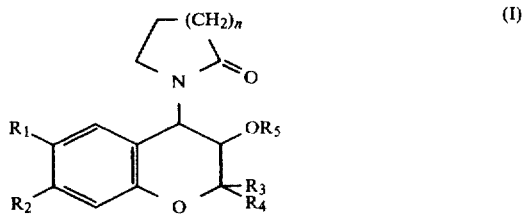

wherein:
one of $R_1$ and $R_2$ is hydrogen and the other is selected from the class of alkylcarbonyl, alkoxycarbonyl, alkylcarbonyloxy, alkylhydroxymethyl, nitro, cyano, chloro, trifluoromethyl, alkylsulphinyl, alkylsulphonyl, alkoxysulphinyl, alkoxysulphonyl, alkylcarbonylamino, alkoxycarbonylamino, or aminosulphinyl, aminosulphonyl or aminocarbonyl, the amino moiety being optionally substituted by one or two alkyl groups, or alkylsulphinylamino, alkylsulphonylamino, alkoxysulphinylamino or alkoxysulphonylamino, or ethylenyl terminally substituted by alkylcarbonyl, nitro or cyano or —C(alkyl)NOH or —C(alkyl)NNH₂, the alkyl groups or alkyl moieties of alkyl-containing groups having from 1 to 6 carbon atoms;
one of $R_3$ and $R_4$ is hydrogen or alkyl having from 1 to 4 carbon atoms and the other is alkyl having from 1 to 4 carbon atoms, or $R_3$ and $R_4$ together with the carbon atom to which they are attached are spiroalkyl having from 3 to 6 carbon atoms;
$R_5$ is hydrogen, alkyl having from 1 to 3 carbon atoms or acyl having from 1 to 8 carbon atoms; and
n is 1 or 2; the lactam group being trans to the $OR_5$ group;
have anti-hypertensive activity and are of use in the treatment of high blood pressure.

25 Claims, No Drawings

BENZOPYRANS

The present invention relates to novel benzopyrans having pharmacological activity, to processes and intermediates for use in their preparation, to pharmaceutical compositions and their preparation, and to their use in the treatment of mammals.

U.S. Pat. No. 4,110,347 describes compounds having blood pressure lowering activity which are of formula (A'):

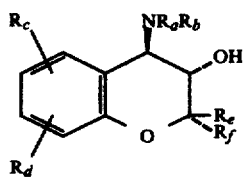

and acid addition salts thereof wherein $R_a$ is a hydrogen atom or a $C_{1-9}$ hydrocarbon group optionally substituted by a hydroxyl or $C_{1-6}$ alkoxyl group; $R_b$ is a hydrogen atom or $C_{1-6}$ alkyl group, or $NR_aR_b$ is a 3-8 membered heterocyclic group optionally substituted by one or two methyl groups; $R_c$ is a hydrogen or halogen atom or a $C_{1-6}$ alkyl, $C_{2-6}$ alkenyl, $C_{1-6}$ alkoxy, $C_{2-6}$ alkenoxyl, $C_{1-6}$ alkylthio, hydroxyl, amino, $C_{1-6}$ alkylamino, $C_{2-6}$ dialkylamino, nitro, trifluoromethyl, $C_{2-7}$ acylamino, $C_{1-6}$ alkoxysulphonylamino, carboxyl, nitrile or $AOR_g$, $ASR_g$, $ASO_2R_g$, $ANHR_g$, $ANR_gCOR_h$, $ANR_gSO_2R_h$ or $ANR_gCO_2R_h$ group wherein A is an alkylene group of 1-4 carbon atoms, $R_g$ is an alkyl group of 1-4 carbon atoms, and $R_h$ is an alkyl group of 1 to 4 carbon atoms; and $R_d$ is a hydrogen or halogen atom or methyl or methoxy, or $R_c$ together with $R_d$ forms a —CH=CH—CH=CH—, —NH—CH=CH—, —CH$_2$—CH$_2$—CH$_2$—CH$_2$— or —CH$_2$—CH$_2$—CH$_2$—CO— system; $R_e$ is a hydrogen atom or a $C_{1-6}$ alkyl or phenyl group; and $R_f$ is a hydrogen atom or a $C_{1-6}$ alkyl or phenyl group.

U.S. Pat. No. 4,251,532 describes compounds having useful anti-hypertensive activity, which are of formula (B'):

wherein $R_i$ is a hydrogen atom or an alkyl group of up to 4 carbon atoms optionally substituted by a chlorine or bromine atom or by a hydroxyl group or by an alkoxyl group of up to 4 carbon atoms or by an acyloxy group of up to 4 carbon atoms and $R_j$ is a hydrogen atom or an alkyl group of up to 4 carbon atoms or $R_i$ is joined to $R_j$ so that together with the nitrogen atom to which they are attached they form a 5-, 6- or 7-membered heterocyclic ring which is optionally substituted by methyl; Y is a group $COR_k$, $CO_2R_k$, $SOR_k$, $SO_2R_k$, $SOOR_k$, $SO_2OR_k$, $CH(OH)R_k$, $C(R_k)$=NOH, $C(R_k)$=NNH$_2$, $CONH_2$, $CONR_lR_m$, $SONR_lR_m$ or $SO_2NR_lR_m$ where $R_k$ and $R_l$ are each independently a hydrocarbon group of up to 8 carbon atoms or such a group inertly substituted by a chlorine or bromine atom or by a hydroxyl group or by an alkoxyl group of 1-4 carbon atoms or by an acyloxy group of up to 4 carbon atoms or by 3 fluorine atoms attached to the same carbon atom and $R_m$ is a hydrogen atom or an alkyl group of up to 4 carbon atoms; and salts thereof and O-acyl derivatives thereof wherein the O-acyl moiety contains up to 18 carbon atoms.

European Patent Publication No. 9912 describes antihypertensive compounds of formula (C'):

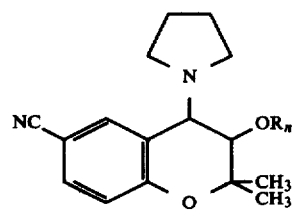

wherein the pyrrolidino and $OR_n$ moities are trans and wherein $R_n$ is a hydrogen atom, an alkyl group of 1 to 3 carbon atoms or an acyl group of 1 to 8 carbon atoms; or a pharmaceutically acceptable acid addition salt thereof.

European Patent Publication No. 28449 describes compounds having blood pressure lowering activity, with low levels of unwanted cardiac effects, which compounds are of formula (D'):

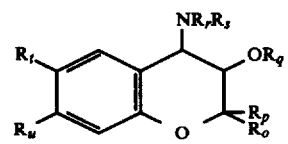

wherein
$R_o$ is a hydrogen atom or a lower alkyl group;
$R_p$ is a hydrogen atom or a lower alkyl group;
$R_q$ is a hydrogen atom or a lower alkyl group;
$R_r$ is a hydrogen atom or a lower alkyl group;
$R_s$ is a lower alkyl or a substituted alkyl group;
or $R_r$ and $R_s$ are joined so that together with the nitrogen atom to which they are attached they form a 5-, 6- or 7-membered ring optionally containing an oxygen or sulphur atom;
$R_t$ is an electron withdrawing group;
$R_u$ is an electron donating group; and the $NR_rR_s$ and $OR_q$ moieties are trans.

European patent publication 28064 describes compounds having blood pressure lowering activity, with low levels of unwanted cardiac effects, which compounds are of formula (E'):

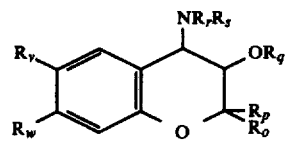

and salts and pro-drugs thereof,
wherein:
$R_o$ $R_p$ $R_q$ $R_r$ and $R_s$ are as defined for formula (D'), and $R_v$ is an electron donating group and $R_w$ is an electron withdrawing group; and the $NR_rR_s$ and $OR_q$ moieties are trans.

It has now been found that a further class of benzopyrans have blood pressure lowering activity. Such compounds are characterised by the presence of an oxo group in the nitrogen-containing ring which substitutes the benzopyran in the 4-position.

Accordingly, the present invention provides a compound of formula (I):

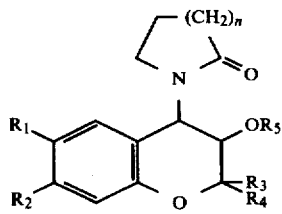
(I)

wherein:
one of $R_1$ and $R_2$ is hydrogen and the other is selected from the class of alkylcarbonyl, alkoxycarbonyl, alkylcarbonyloxy, alkylhydroxymethyl, nitro, cyano, chloro, trifluoromethyl, alkylsulphinyl, alkylsulphonyl, alkoxysulphinyl, alkoxysulphonyl, alkylcarbonylamino, alkoxycarbonylamino or aminosulphinyl, aminosulphonyl or aminocarbonyl, the amino moiety being optionally substituted by one or two alkyl groups, or alkylsulphinylamino, alkylsulphonylamino, alkoxysulphinylamino or alkoxysulphonylamino or ethylenyl terminally substituted by alkylcarbonyl, nitro or cyano, or —C(alkyl)NOH or —C(alkyl)NNH$_2$, the alkyl groups or alkyl moieties of alkyl-containing groups having from 1 to 6 carbon atoms;
one of $R_3$ and $R_4$ is hydrogen or alkyl having from 1 to 4 carbon atoms and the other is alkyl having from 1 to 4 carbon atoms, or $R_3$ and $R_4$ together with the carbon atom to which they are attached are spiroalkyl having from 3 to 6 carbon atoms;
$R_5$ is hydrogen, alkyl having from 1 to 3 carbon atoms or acyl having from 1 to 8 carbon atoms; and
n is 1 or 2; the lactam group being trans to the OR$_5$ group.

The other of $R_1$ and $R_2$, when one of them is hydrogen, is preferably selected from the class of alkylcarbonyl, alkoxycarbonyl, alkylcarbonyloxy, alkylhydroxymethyl, nitro or cyano.

The alkyl groups or alkyl moieties of alkyl-containing groups, in respect of the other of $R_1$ and $R_2$, are preferably methyl or ethyl.

$R_3$ and $R_4$ are preferably both alkyl having from 1 to 4 carbon atoms. In particular they are both methyl or ethyl, preferably both methyl.

When $R_5$ is alkyl, preferred examples thereof include methyl, ethyl and n-propyl, of which methyl is most preferred. When $R_5$ is acyl, a preferred class is unsubstituted carboxylic acyl, such as aliphatic acyl or benzoyl. $R_5$ however is preferably hydrogen.

Within formula (I) is a sub-group of preferred compounds of formula (II):

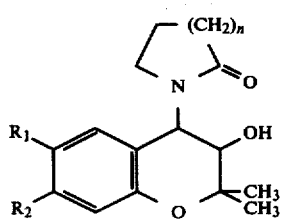
(II)

wherein one of $R_1$ and $R_2$ is hydrogen and the other is selected from the class of alkylcarbonyl, alkoxycarbonyl, alkylcarbonyloxy, alkylhydroxymethyl, nitro or cyano, the alkyl groups or alkyl moieties of alkyl containing groups being methyl or ethyl, and n is 1 or 2.

Compounds of formula (II), wherein one of $R_1$ and $R_2$ is hydrogen and the other is nitro or cyano, are greatly preferred. Additionally, compounds of formula (II), wherein $R_2$ is hydrogen and $R_1$ is one of the substituents as defined hereinbefore, are preferred. Consequently the most preferred compounds are those wherein $R_1$ is nitro or cyano and $R_2$ is hydrogen.

The compounds of formula (I) and (II) cover both a piperidone substituent (when n=2) and a pyrrolidone substituent (when n=1).

It is preferred that the compounds of formula (I) and (II) are in substantially pure form.

The present invention extends to the compounds of formulae (I) and (II) whenever prepared synthetically.

The compounds of formulae (I) and (II) have asymmetric centres and therefore exist in optically active forms. The present invention extends to all such forms individually and to mixtures of them.

The present invention also provides a process for the preparation of a compound of formula (I), which comprises cyclising a compound of formula (III), or when $R_5$ is hydrogen a metal salt thereof;

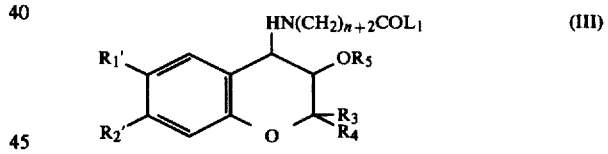
(III)

wherein one of $R_1'$ and $R_2'$ is hydrogen or a group or atom convertible into hydrogen and the other is one of the class of substituents as defined hereinbefore for the other of $R_1$ and $R_2$ or a group or atom convertible thereto, $R_3$ to $R_5$ and n are as defined hereinbefore, $L_1$ is a leaving group; and wherein the substituted amino group is trans to the OR$_5$ group; in the case when one of $R_1'$ and $R_2'$ is a group or atom convertible into hydrogen, converting the group or atom into hydrogen; in the case when the other of $R_1'$ and $R_2'$ is a group or atom convertible into one of the class of substituents as defined hereinbefore for the other of $R_1$ and $R_2$, converting the group or atom into one of the class of substituents as defined; and, in the case when $R_5$ is hydrogen in the compound of formula (I), optionally alkylating or acylating with an alkylating agent having from 1 to 3 carbon atoms or an acylating agent having from 1 to 8 carbon atoms.

The leaving group $L_1$ is a group that is displaceable by a secondary amino nucleophile. Preferred examples of such groups include hydroxy and, in particular, $C_{1-4}$ alkoxy, such as ethoxy.

The cyclisation is normally carried out by heating the compound of formula (III) under reflux in an inert solvent, such as xylene or toluene.

When a metal salt of formula (III) is used, the sodium salt is preferred. However, it is even more preferred not to use a metal salt at all, especially as any elimination side reactions are thereby avoided.

Conversions of an aromatic group or atom into one of the class of substituents as defined hereinbefore for the other of $R_1$ and $R_2$, when one of them is hydrogen, are generally known. For example, it is preferred, when carrying out the reaction, to protect any unsubstituted terminal amino moieties, such as when the other of $R_1$ and $R_2$ is aminosulphinyl, aminosulphonyl or aminocarbonyl, with a protecting agent. Examples of protecting agents include acyl groups, such as acetyl. Protection of the unsubstituted terminal amino moiety is carried out by reacting a compound of formula (III), wherein one of $R_1'$ and $R_2'$ is hydrogen and the other is aminosulphinyl, aminosulphonyl or aminocarbonyl, with, for example, an acyl chloride. Removal of the acyl protecting agent is carried out by base hydrolysis after the cyclising reaction.

Conversions of an aromatic group or atom into one of the class of substituents as defined hereinbefore for the other $R_1$ and $R_2$, when one of them is a group or atom convertible into hydrogen, are generally known as well. For example, a hydrogen atom may be replaced by a nitro group by nitrating in a known manner a compound of formula (III), wherein one of $R_1'$ and $R_2'$ is hydrogen and the other is acetamido, followed by hydrolysing the compound, converting the resulting amine into a diazonium salt, and finally decomposing it, leaving a compound of formula (I), wherein one of $R_1$ and $R_2$ is hydrogen and the other is nitro.

It is however preferred that any conversions are carried out at an earlier stage as mentioned hereinafter.

Preferably, the alkylating agent is an alkyl iodide, the reaction being carried out in an inert solvent, such as toluene, in the presence of a base, such as potassium t-butoxide.

Preferably, the acylating agent is a carboxylic acid or a derivative thereof, such as an anhydride, the reaction being carried out in a non-hydroxylic solvent in the presence of a condensation promoting agent, such as dicyclohexyl-carbodiimide.

Compounds of formula (III) can be prepared by reacting a compound of formula (IV):

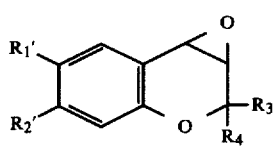
(IV)

wherein $R_1'$ and $R_2'$ and $R_3$ and $R_4$ are as defined hereinbefore, with a compound of formula (V):

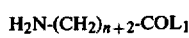

$H_2N-(CH_2)_{n+2}-COL_1$ (V)

wherein n and $L_1$ are as defined hereinbefore.

The reaction is normally carried out in a solvent at low, medium or high temperature. The solvent may be an alcohol, such as methanol or ethanol.

When $L_1$ is hydroxy the reaction proceeds well if carried out in refluxing ethanol in the presence of aqueous sodium carbonate. When $L_1$ is $C_{1-4}$ alkoxy, the reaction is preferably carried out in the presence of sodium hydroxide in ethanol.

Under some conditions, the compound of formula (III) spontaneously cyclises to form a compound of formula (I).

Compounds of formula (IV) can be prepared, preferably in situ, by reacting a compound of formula (VI):

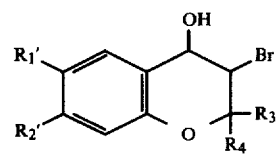
(VI)

wherein $R_1'$ and $R_2'$ and $R_3$ and $R_4$ are as defined hereinbefore and the hydroxy group is trans to the bromo atom, with a base, such as potassium hydroxide, in ether or aqueous dioxan.

Alternatively, compounds of formula (III) can be prepared by reacting a compound of formula (VII):

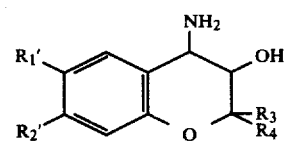
(VII)

wherein $R_1'$, $R_2'$, $R_3$ and $R_4$ are as defined hereinbefore, and the amino group is trans to the hydroxy group, with a compound of formula (VIII):

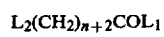

$L_2(CH_2)_{n+2}COL_1$ (VIII)

wherein n and $L_1$ are as defined hereinbefore and $L_2$ is a leaving group.

The leaving group, $L_2$, is a group that is displaceable by a primary amino nucleophile. Preferred examples of such groups include halo, such as chloro and bromo.

Compounds of formula (VII) can be prepared by a reaction of a compound of formula (IV) with ethanolic ammonium hydroxide solution. Alternatively, they can be prepared by reduction with zinc and hydrochoric acid of a compound of formula (IX):

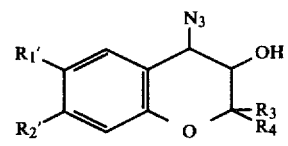
(IX)

wherein $R_1'$, $R_2'$, $R_3$ and $R_4$ are as defined hereinbefore and wherein the azide group is trans to the hydroxy group.

Compounds of formula (IX) can in turn be prepared from a compound of formula (IV) by reaction with sodium azide in the presence of boric acid in for example dimethylformamide.

The present invention provides another process for the preparation of a compound of formula (I), which comprises oxidising a compound of formula (X), or when $R_5$ is hydrogen a metal salt thereof:

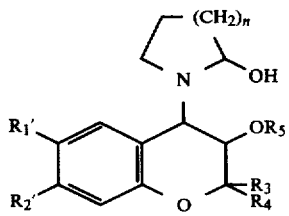
(X)

wherein $R_1'$, $R_2'$, $R_3$, to $R_5$ and n are as defined hereinbefore, and wherein the nitrogen-containing ring is trans to the $OR_5$ group; in the case when one of $R_1'$ and $R_2'$ is a group or atom convertible into hydrogen, converting the group or atom into hydrogen; in the case when the other of $R_1'$ and $R_2'$ is a group or atom convertible into one of the class of substituents as defined hereinbefore for the other of $R_1$ and $R_2$, converting the group or atom into one of the class of substituents as defined; and, in the case when $R_5$ is hydrogen in the compound of formula (I), optionally alkylating or acylating with an alkylating agent having from 1 to 3 carbon atoms or an acylating agent having from 1 to 8 carbon atoms.

The oxidation is preferably carried out in a solvent such as aqueous methanol with a metal periodate such as potassium periodate.

Compounds of formula (X) can be prepared by cyclising in the presence of an acid a compound of formula (XI):

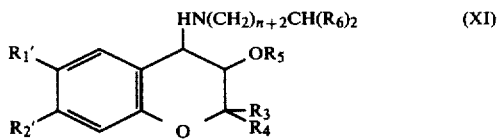
(XI)

wherein $R_6$ is methoxy or ethoxy and $R_1'$, $R_2'$, $R_3$ to $R_5$ and n are as defined hereinbefore and wherein the substituted amino group is trans to the $OR_5$ group.

Compounds of formula (XI) can in turn be prepared by reacting a compound of formula (IV) with a compound of formula (XII):

$$H_2N(CH_2)_{n+2}CH(R_6)_2 \quad (XII)$$

wherein n $R_6$ and is as defined hereinbefore.

The present invention provides a further process for the preparation of a compound of formula (I), which comprises reacting a compound of formula (IV) with an anion of formula (XIII):

(XIII)

wherein n is as defined hereinbefore; in the case when one of $R_1'$ and $R_2'$ is a group or atom convertible into hydrogen, converting the group or atom into hydrogen; in the case when the other of $R_1'$ and $R_2'$ is a group or atom convertible into one of the class of substituents as defined hereinbefore for the other of $R_1$ and $R_2$, converting the group or atom into one of the class of substituents as defined; and, in the case when $R_5$ is hydrogen in the compound of formula (I), optionally alkylating or acylating with an alkylating agent having from 1 to 3 carbon atoms or an acylating agent having 1 to 8 carbon atoms.

The reaction is preferably carried out in a solvent such as dimethylsulphoxide in the presence of a base, such as sodium hydride.

The compound of formula (IV) can be prepared in situ from the corresponding compound of formula (VI). In such circumstances, it is advantageous not to add the lactam of formula (XIII) until sufficient time has elapsed for the epoxide of formula (IV) to be produced.

The present invention provides yet another process for the preparation of a compound of formula (I), which comprises cyclising a compound of formula (XIV):

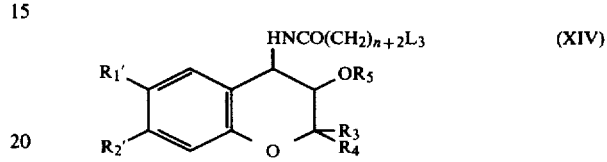
(XIV)

wherein $R_1'$, $R_2'$, $R_3$ to $R_5$ and n are as defined hereinbefore and $L_3$ is a leaving group, and wherein the substituted amino group is trans to the $OR_5$ group; in the case when one of $R_1'$ and $R_2'$ is a group or atom convertible into hydrogen, converting the group or atom into hydrogen; in the case when the other of $R_1'$ and $R_2'$ is a group or atom convertible into one of the class of substituents as defined hereinbefore for the other of $R_1$ and $R_2$, converting the group or atom into one of the class of substituents as defined; and, in the case when $R_5$ is hydrogen in the compound of formula (I), optionally alkylating or acylating with an alkylating agent having from 1 to 3 carbon atoms or an acylating agent having from 1 to 8 carbon atoms.

The leaving group $L_3$, is a group that is displaceable by a secondary amino nucleophile adjacent to a carbonyl function. A preferred example is chloro.

The cyclisation reaction is preferably carried out in a solvent such as dimethylformamide in the presence of a base, such as sodium hydride.

Compounds of formula (XIV) can be prepared by reacting a compound of formula (VII) with a compound of formula (XV):

$$L_3(CH_2)_{n+2}COL_4 \quad (XV)$$

wherein $L_3$ and n are as defined hereinbefore and $L_4$ is a leaving group; and optionally alkylating or acylating with an alkylating agent having from 1 to 3 carbon atoms or an acylating agent having from 1 to 8 carbon atoms.

The leaving group, $L_4$, is a group that, when adjacent to a carbonyl function, is displaceable by a primary amino nucleophile.

The reaction is preferably carried out in a solvent, such as chloroform or methylene chloride, in the presence of aqueous base, such as aqueous sodium hydroxide.

In the reactions with the epoxide of formula (IV), the trans isomer is specifically formed.

Compounds of formula (VI) can be prepared in accordance with known processes, for example the process described in the aforementioned U.S. patents and European patent publications. Schematically, such process can be depicted thus:

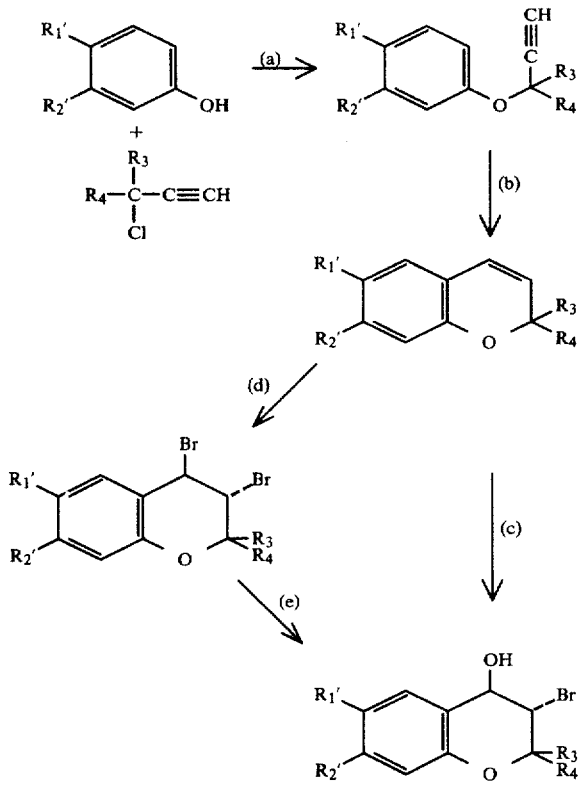

(a) Room temperature; NaOH/40% benzyltrimethylammonium hydroxide in methanol;
(b) Heat in o-dichlorobenzene;
(c) N—bromosuccinimide/dimethylsulphoxide/water;
(d) Bromine in carbon tetrachloride; and
(e) Acetone/water.

The above process can produce mixtures of compounds during reaction (b) owing to the two sites available for ring formation. It is therefore advisable to remove any of the undesired compound by, for example, chromatography, before reaction (c) or or (d).

Instead of carrying out the conversion of a group or atom into hydrogen or group or atom into one of the class of substituents defined for the other of $R_1$ and $R_2$ after cyclising a compound of formula (III) or (XIV), or after oxidising a compound of formula (X), or after reacting a compound of formula (IV) with an anion of formula (XIII), it is greatly preferred that any such conversions are carried out at an earlier stage, preferably on the chromene produced after reaction (b) above. In other words, it is preferred that, for the processes of the invention $R_1'$ and $R_2'$ and $R_1$ and $R_2$ respectively.

As mentioned previously, the compounds of formula (I) exist in optically active forms, and the processes of the present invention produce mixtures of such forms. The individual isomers may be separated one from another by chromatography using a chiral phase. Alternatively, an asymmetric synthesis would offer a route to the individual form.

It is preferred that the compounds of formula (I) are isolated in substantially pure form.

The intermediates of formula (III), (IX), (X), (XI) and (XIV) are novel and constitute part of the invention.

As mentioned previously, the compounds of formula (I), and especially those of formula (II), have been found to have blood-pressure lowering activity. They are therefore useful as a pharmaceutical in the treatment of hypertension.

The present invention accordingly provides apharmaceutical composition which comprises a compound of this invention and a pharmaceutically acceptable carrier. In particular, the present invention provides an antihypertensive pharmaceutical composition which comprises an anti-hypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit-dose. Suitable unit dose forms include tablets, capsules and powders in sachets or vials. Such unit dose forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

The compositions of the invention may be formulated with conventional excipients, such as a filler, a disintegrating agent, a binder, a lubricant, a flavouring agent and the like. They are formulated in conventional manner, for example in a manner similar to that used for known anti-hypertensive agents, diuretics and $\beta$-blocking agents.

The present invention further provides a compound of formula (I) and especially of formula (II) for use in the treatment of hypertension.

The present invention yet further provides a method of treating hypertension in mammals including man, which comprises administering to the suffering mammal an anti-hypertensive effective amount of a compound of formula (I) or a pharmaceutical composition of the invention.

The following descriptions relate to the preparation of intermediates and the following examples relate to the preparation of a compound of formula (I).

DESCRIPTION 1

6-Cyano-3,4-dihydro-2,2-dimethyl-3,4-epoxy-2H-benzo[b]-pyran

4-Cyanophenol (19.60 g), sodium hydroxide (9.90 g), 40% benzyltrimethylammonium hydroxide in methanol (34.50 g) and 3-methyl-3-chlorobutyne (25.50 g) were stirred in water (150 ml) and dichloromethane (150 ml) for 5.5 days at room temperature. After separation of the layers, the aqueous layer was extracted twice with chloroform, and the combined organic phase evaporated leaving a gum which was taken up in ether and washed three times with 10% sodium hydroxide solution and with water before drying over magnesium sulphate. Removal of drying agent and solvent gave a viscous liquid having absorptions in the IR (film) at 2100, 2220, 3290 cm$^{-1}$. This liquid (20.91 g) was heated in o-dichlorobenzene (40 ml) at reflux temperature for 1.5 hours under nitrogen. After distillation of the solvent the fraction boiling at 110°–114°/0.02 mmHg (16.57 g) was collected, which on standing formed a low melting solid, having an IR absorption at 2230 cm$^{-1}$. (See M. Harfenist and E. Thom, *J. Org. Chem.*, 841 (1972) who quote m.p. 36°–37°).

Addition to this 6-cyanochromene (16.50 g) dissolved in dimethyl sulphoxide (150 ml) containing water (3.24 ml) of N-bromosuccinimide (31.90 g) with vigorous stirring and cooling, followed by dilution with water and extraction via ethyl acetate gave a mixture which was boiled in acetone (300 ml) and water (100 ml) for 5 hours to hydrolyse the small amount of 3,4-dibromide present. Evaporation of solvents gave 6-cyano-trans-3-bromo-3,4-dihydro-2,2-dimethyl-2H-benzo[b]pyran-4-ol as white crystals (24.37 g). A small sample had m.p. 128°–128.5° from 60°–80° petroleum ether, nmr (CDCl$_3$)δ1.43 (3H), 1.62 (3H), 7.48 (1H, exchangeable), 4.07 (1H, d, J=9), 4.87 (1H, d, J=9), 6.80 (1H, d, J=8), 7.43 (1H, q, J=8, 2), 7.78 (1H, d, J=2). Analysis calculated for C$_{12}$H$_{12}$NO$_2$Br:C, 51.07; H, 4.26; N, 4.96; Br, 28.37. Found: C, 50.95; H, 4.38; N, 5.03; Br, 28.39%.

The bromohydrin (24.30 g) was stirred with sodium hydroxide pellets (5.00 g) in water (250 ml) and dioxan (200 ml) for 3 hours at room temperature. The solvents were removed by distillation under high vacuum and the residue taken up in ether and washed with water and brine before drying over magnesium sulphate. Removal of drying agent and solvent and gave crude 6-cyano-3,4-dihydro-2,2-dimethyl-3,4-epoxy-2H-benzo[b]pyran (16.02 g) as a gum, having an absorption at 2230 cm$^{-1}$ in the IR and Nmr (CCl$_4$)δ1.26 (3H), 1.54 (3H), 3.40 and 3.80 (each 1H, d, J=4), 6.77 (1H, d, J=8), 7.43 (1H, q, J=8, 2), 7.58 (1H, d, J=2).

DESCRIPTION 2

6-Cyano-3,4-dihydro-2,2-dimethyl-trans-4-amino-2H-benzo[b]pyran-3-ol

The title compound was prepared by stirring 6-cyano-3,4-dihydro-2,2-dimethyl-3,4-epoxy-2H-benzo[b]pyran in ethanolic ammonium hydroxide solution at room temperature until thin layer chromatography showed consumption of the starting epoxide.

DESCRIPTION 3

6-Cyano-3,4-dihydro-2,2-dimethyl-trans-4-(1-keto-4-chlorobutylamino)-2H-benzo[b]pyran-3-ol The amino chromanol (1.40 g), as obtained in Description 2, was stirred in chloroform (20 ml) and water (10 ml) containing sodium hydroxide pellets (0.26 g) at room temperature. 4-Chlorobutyryl chloride (0.72 ml) was added and the reaction stirred vigorously for 0.5 hours. Separation of the layers and washing the organic layer with water, then brine, drying over magnesium sulphate, filtration and evaporation gave the title compound as a pale yellow solid.

DESCRIPTION 4

6-Cyano-3,4-dihydro-2,2-dimethyl-trans-4-(4,4-diethoxybutylamino)-2H-benzo[b]pyran-3-ol 6-Cyano-3,4-dihydro-2,2-dimethyl-3,4-epoxy-2H-benzo[b]pyran (200 mg) and 4-aminobutyraldehyde diethylacetal (200 mg) were heated to 100° C. for 1.5 hours, a clear yellow solution forming during this time. After cooling, dilution with ether, and washing successively with water and brine, drying over sodium sulphate and evaporation, the aminoacetal was obtained as a pale yellow oil (291 mg).

DESCRIPTION 5

6-Cyano-3,4-dihydro-2,2-dimethyl-trans-4-(2-hydroxy-1-pyrrolidinyl)-2H-benzo[b]pyran-3-ol The oily acetal, as obtained in Description 4, was dissolved in dioxan (2 ml) and treated with 2.5 M HCl (1 ml). After 30 minutes the reaction was diluted with ether and neutralised with sodium carbonate solution.

The two phases were separated, the aqueous layer further extracted with ether and the combined extracts washed with water and brine and dried over sodium sulphate. The organic phase was filtered and applied to Kieselgel 60 (10 g) and diluted with ethyl acetate-heptane-triethyl-amine (10:20:2). Three fractions were obtained (total 128 mg) containing the title compound. TLC (silica gel; ethyl acetate-heptane-triethylamine (10:20:2) showed the presence of varying amounts of the two positional isomers in each fraction.

IR (KBr disc) 3450, 2230 cm$^{-1}$ for all three fractions.

Mass spectrum (Isobutane and ammonium C.I.) showed m/z 271 (MH$^+$-H$_2$O) for all three fractions.

DESCRIPTION 6

6-Nitro-3,4-dihydro-2-methyl-3,4-epoxy-2H-benzo[b]pyran p-Nitrophenol (49.3 g), 3-bromobut-1-yne (39.0 g), potassium carbonate (66 g) and potassium iodide (3.1 g) were heated and stirred under nitrogen for 20 hours. The mixture was cooled, filtered, and evaporated and the residue taken up in ether and washed with sodium hydroxide solution (10%) before drying over magnesium sulphate. Filtration and evaporation gave the phenoxybutyne as a yellow oil (39.03 g). This crude phenoxybutyne (30 g) was heated in o-dichlorobenzene (1 liter) for 24 hours under nitrogen. Removal of solvent, and recrystallisation from 60°–80° petroleum ether gave 2-methyl-6-nitrochromene as an oily solid. The nitrochromene (6.10 g) dissolved in dimethyl sulphoxide (50 ml) containing water (1.12 ml) was treated with N-bromosuccinimide (11.40 g) in one portion with vigorous stirring. After 0.5 hours the reaction mixture was poured into water (500 ml) and extracted with ethyl acetate to yield the bromohydrin (7.4 g) as a sticky solid. Recrystallisation from ethyl acetate-petroleum ether gave a sample of m.p. 159°. The bromohydrin (2.27 g) was stirred with potassium hydroxide pellets (2.2 g) in ether (500 ml) for 48 hours. Filtration gave the 3,4-epoxy-2-methylchroman as a yellow crystalline solid (1.05 g).

DESCRIPTION 7

6-Nitro-3,4-dihydro-2-methyl-trans-4-(ethoxycarbonylpropylamino)-2H-benzo[b]-pyran-3-ol The epoxide of Description 6 (1.03 g) was boiled with ethyl 4-aminobutyrate hydrochloride (0.84 g) and sodium hydroxide pellets (0.20 g) in ethanol (50 ml) for 10 hours. Filtration and evaporation and chromatographic purification gave a gum (1.10 g) which was dissolved in 2 N hydrochloric acid and extracted three times with ethyl acetate. Basification of the aqueous phase and extraction with ethyl acetate gave a crude ester which was used as such in Example 9.

DESCRIPTION 8

7-Nitro-3,4-dihydro-2,2-dimethyl-trans-4-(3-carbethoxypropylamino)-2H-benzo[b]pyran-3-ol 7-Nitro-3,4-dihydro-2,2-dimethyl-3,4-epoxy-2H-benzo[b]pyran (0.48 g, the preparation of which is described in Example 3 of U.K. Pat. No. 1,548,221), ethyl 4-aminobutyrate hydrochloride (0.34 g) and sodium hydroxide pellets (0.08 g) were refluxed in ethanol (50 ml) for 12 hours. Filtration and evaporation and chromatography on a chromatotron (2 mm silica gel $HF_{254}$, gradient elution with pentane-ethyl acetate) gave recovered epoxide (0.20 g) and trans-4-(3-carbethoxypropylamino)-7-nitro-2,2-dimethyl-2H-benzo[b]pyran-3-ol (0.21 g) as a gum, which was used as such in Example 10.

DESCRIPTION 9

6-Chloro-3,4-dihydro-2,2-dimethyl-trans-3-bromo-4-hydroxy-2H-benzo[b]pyran

The title compound was prepared analogously to the preparation of the 3-bromo-4-hydroxy compound of Description 1 giving a crude crystalline solid.

NMR (CDCl$_3$): δ1.35 (3H, s), 1.53 (3H, s), 3.22 (1H, m), 4.00 (1H, d, J=9 Hz), 4.77 (1H, d, J=9 Hz), 6.51 (1H, d, J=8 Hz), 7.03 (1H, q, J=8.2 Hz), 7.30 (1H, narrow m).

DESCRIPTION 10

6-Chloro-3,4-dihydro-2,2-dimethyl-3,4-epoxy-2H-benzo-[b]pyran

The crude crystalline solid (10.27 g) of Description 9 was dissolved in dimethyl sulphoxide (50 ml) and treated with sodium hydride (1.06 g, 80% dispersion on oil) over a period of an hour. The resulting material was used as such immediately in Example 12.

EXAMPLE 1

6-Cyano-3,4-dihydro-2,2-dimethyl-trans-4-(2-oxo-1-pyrrolidinyl)-2H-benzo-[b]-pyran-3-ol (E1)

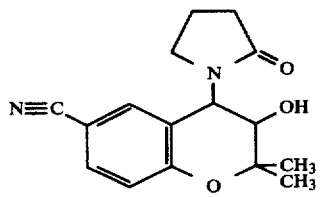

(E1)

6-Cyano-3,4-dihydro-2,2-dimethyl-3,4-epoxy-2H-benzo-[b]-pyran (0.50 g), as obtained in Description 1, 4-aminobutyric acid (1.25 g) and sodium bicarbonate (1.00 g) were refluxed in ethanol (15 cc) and distilled water (2.5 cc) for 10 hours. The reaction was filtered and evaporated and the residue chromatographed on 25 g Kieselgel 60. Elution with MeOH-chloroform (1:3) gave 132 mg of the most polar product. This was refluxed in toluene (10 cc) for 2 hours, cooled and the solvent evaporated. The residue was chromatographed on 5 g Kieselgel 60 and eluted with MeOH-chloroform (1:3) to give the title compound as a white solid (90 mg), m.p. 230°-231°.

IR (KBr disc): 3260, 2220, 1651 cm$^{-1}$;

NMR (CDCl$_3$) δ1.28 (3H); 1.55 (3H); 2.11 (2H, m); 2.57 (2H, m); 3.22 (3H, 1 exchangeable H, broad m); 3.64 (1H, d, J=10); 5.26 (1H, d, J=10); 6.87 (1H, d, J=9); 7.24 (1H, narrow m); 7.45 (1H, q, J=9, 2);

Analysis calculated for $C_{16}H_{18}N_2O_3$: C,67.12;H,6.34;N,9.78%  Found C,66.83;H,6.17;N,9.50%

EXAMPLE 2

6-Cyano-3,4-dihydro-2,2-dimethyl-trans-4-(2-oxo-1-pyrrolidinyl)-2H-benzo-[b]-pyran-3-ol of formula (E1)

6-Cyano-3,4-dihydro-2,2-dimethyl-3,4-epoxy-2H-benzo-[b]-pyran (1.00 g), as obtained in Description 1, ethyl-4-aminobutyrate hydrochloride (0.84 g), ethanol (50 ml) and sodium hydroxide pellets (0.20 g) were stirred at room temperature for 8 days, then at 40° for 3 hours. After cooling and evaporation the residue was taken up in ethyl acetate and filtered. Evaporation of the filtrate gve a gum (1.46 g) which was chromatographed using a chromatotron (2 mm silica gel $HF_{254}$ plate; 2 runs; solvent flow rate 6 ml/min.). Elution with 2% methanol-chloroform mixture gave starting epoxide (0.23 g) followed by a more polar ester fraction (0.64 g), and a mixture (0.15 g) which on further chromatography under identical conditions gave 6-cyano-3,4-dihydro-2,2-dimethyl-trans-4-(2-oxo-1-pyrrolidinyl)-2H-benzo[b]pyran-3-ol having an identical NMR spectrum to that obtained in Example 1.

A portion of the ester fraction (150 mg) was dissolved in ether containing a little ethanol and treated with anhydrous ethanolic HCl. The precipitate was collected and triturated with ether to give trans-4-(3-carbethoxypropylamino)-6-cyano-2,2-dimethyl-2H-benzo[b]pyran-3-ol hydrochloride (138 mg) of m.p. 198°-200°.

NMR (CD$_3$OD): 1.23 (s, 3H) overlapped with; 1.26 (t, J=8, 8 3H); 1.58 (s, 3H); 2.19 (m, 2H); 2.53 (m, 2H); 2.85-3.45 (irreg. m, 2H); 4.02 (d, J=10, 1H) overlapped with 4.16 (q, J=8, 8, 8 2H) and 3.75-4.65 (m, 3H, exchangeable); 4.53 (3, J=10, 1H); 7.00 (d, J=9, 1H); 7.60 (q, J=9, 2, 1H); 8.15 (d, J=2, 1H);

Analysis calculated for $C_{18}H_{25}N_2O_4$: C,58.61;H,6.83;N,7.59%  Found: C,58.55;H,6.80;N,7.29%.

The remainder of the ester fraction was heated under reflux in xylene (50 ml) for 7.25 hours. The solution was cooled and filtration gave 6-cyano-3,4-dihydro-2,2-dimethyl-trans-4-(2-oxo-1-pyrrolidinyl)-2H-benzo[b]-pyran-3-ol (425 mg) as crystals of m.p. 226° having an identical NMR spectrum and t.l.c. characteristics as the compound of Example 1.

EXAMPLE 3

6-Cyano-3,4-dihydro-2,2-dimethyl-trans-4-(2-oxo-1-pyrrolidinyl)-2H-benzo[b]pyran-3-ol of formula (E1)

6-Cyano-3,4-dihydro-2,2-dimethyl-trans-4-(1-keto-4-chlorobutylamino)-2H-benzo[b]pyran-3-ol (0.76 g), as obtained in Description 3, in dry tetrahydrofuran (10 ml) was added to a suspension of sodium hydride (0.15 g) in tetrahydrofuran (20 ml) and the reaction stirred under nitrogen for 3 hours. Addition of water and extraction via ethyl acetate gave 540 mg of the title compound having an identical NMR spectrum and tlc characteristics as the compound of Example 1.

EXAMPLE 4

6-Cyano-3,4-dihydro-2,2-dimethyl-trans-4-(2-oxo-1-pyrrolidinyl)-2H-benzo[b]pyran-3-ol of formula (E1)

A solution of 6-cyano-3,4-dihydro-2,2-dimethyl-trans-3-bromo-4-hydroxy-2H-benzo[b]pyran (4 g, 14.2 mM) in dimethylsulphoxide (20 ml) was stirred and sodium hydride (60% dispersion in oil, 0.6 g, 15 mM) added. The suspension was stirred for 1 hour when a solution of 6-cyano-3,4-dihydro-2,2-dimethyl-3,4-epoxy-2H-benzo[b]pyran resulted. 2-Pyrrolidone (1.8 g, 21 mM) and further sodium hydride (0.8 g, 21 mM) were introduced and the mixture stirred at room temperature for an additional 16 hours. Water (40 ml) was slowly added to the mixture to induce crystallisation of the product after which it was cooled in ice and filtered under suction. Crystallisation from ethanol (20 ml) gave the title compound as a cream coloured solid in 60% yield. Recrystallisation from ethyl acetate afforded the pure product as needles, m.p. 226.5°-227.5° having an nmr spectrum and t.l.c. characteristics identical to those of the compound of Example 1.

EXAMPLE 5

6-Carbomethoxy-3,4-dihydro-2,2-dimethyl-trans-4-(2-oxo-1-pyrrolidinyl)-2H-benzo[b]pyran-3-ol (E5)

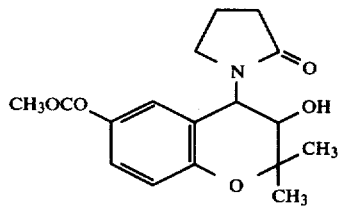

(E5)

6-Carbomethoxy-3,4-dihydro-2,2-dimethyl-3,4-epoxy-2H-benzo[b]pyran (2.42 g, the preparation of which is described in Example 4 of U.K. Pat. No. 1,511,187) and 2-pyrrolidone (0.88 g), were stirred in dimethyl sulphoxide (40 ml) under nitrogen at room temperature. Sodium hydride (0.31 g, 81% dispersion in mineral oil) was added during 5 mins. and the reaction stirred for a further 6 hours. Addition of water, extraction with ethyl acetate, drying or the organic phase with magnesium sulphate, filtration, evaporation and recrystallisation from ethyl acetate-pentane gave 6-carbomethoxy-3,4-dihydro-2,2-dimethyl-trans-4-(2-oxo-1-pyrrolidinyl)-2H-benzo[b]-pyran-3-ol of m.p. 190°-192°.

NMR (CDCl$_3$ soln+1 drop D$_2$O): $\delta$1.30 (3H, s) 1.55 (3H, s) 1.75-2.30 (2H, m) 2.60 (2H, irregular t, J=8 Hz) 2.80-3.40 (2H, m) 3.74 (1H, d, J=10 Hz) 3.87 (3H, s) 5.33 (1H, d, J=10 Hz) 6.86 (1H, d, J=8 Hz) 7.67 (1H, narrow m) 7.88 (1H, q, J=8, 2 Hz).

EXAMPLE 6

6-Carbomethoxy-3,4-dihydro-2,2-dimethyl-trans-4-(2-oxo-1-piperidinyl)-2H, benzo[b]pyran-3-ol (E6)

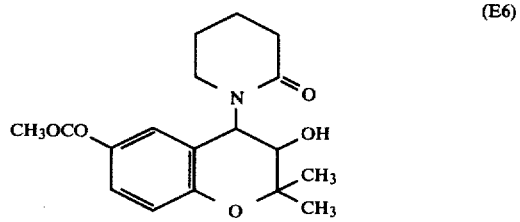

(E6)

In a similar manner to that described in Example 5 employing 2-piperidone in place of 2-pyrrolidone, 6-carbomethoxy-3,4-dihydro-2,2-dimethyl-trans-4-(2-oxo-1-piperidinyl)-2H-benzo[b]-pyran-3-ol was prepared as crystals of m.p. 249°-250° from ethyl acetate.

NMR (CDCl$_3$ soln+1 drop D$_2$O): $\delta$1.27 (3H, s) 1.52 (3H, s) 1.65-2.05 (4H, m) 2.60 (2H, irregular t, J=7 Hz) 2.85-3.15 (2H, m) 3.77 (1H, d, J=10 Hz) 3.88 (3H, s) 5.94 (1H, d, J=10 Hz) 6.86 (1H, d, J=8 Hz 7.71 (1H, narrow m) 7.87 (1H, q, J=8, 2 Hz).

EXAMPLE 7

6-Cyano-3,4-dihydro-2,2-dimethyl-trans-4-(2-oxo-1-piperidinyl)-2H-benzo[b]pyran-3-ol (E7)

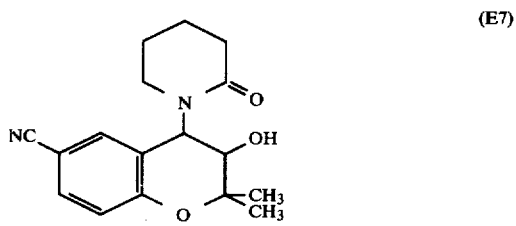

(E7)

In a similar manner to that described in Example 5 employing 2-piperidone in place of 2-pyrrolidone and 6-cyano-3,4-dihydro-2,2-dimethyl-3,4-epoxy-2H-benzo[b]pyran in place of the corresponding 6-carbomethoxy compound, 6-cyano-3,4-dihydro-2,2-dimethyl-trans-4-(2-oxo-1-piperidinyl)-2H-benzo[b]pyran-3-ol was prepared, as crystals of m.p. 155° from ethyl acetate.

IR (KBr disc) 3480, 2212, 1612 cm$^{-1}$;

NMR (CDCl$_3$ soln): $\delta$1.25 (3H, s) 1.50 (3H, s) 1.63-2.10 (4H, m) 2.36-2.76 (2H, m) 3.72 (1H, d, J=10 Hz) 3.90-4.20 (1H, exchangeable, m) 5.72 (1H, d, J=10 Hz) 6.76 (1H, d, J=8 Hz) 7.17 (1H, m, narrow) 7.42 (1H, q, J=8, 2 Hz).

EXAMPLE 8

6-Cyano-3,4-dihydro-2,2-dimethyl-trans-4-(2-oxo-1-pyrrolidinyl)-2H-benzo[b]pyran-3-ol of formula (E1)

6-Cyano-3,4-dihydro-2,2-dimethyl-trans-4-(2-hydroxy-1-pyrrolidinyl)-2H-benzo[b]pyran-3-ol (5 mg), as obtained in Description 5, dissolved in methanol-water (1 ml) was treated with an excess of sodium periodate with stirring during 15 hours at room temperature. Evaporation of solvents and extraction by ethyl acetate gave material having identical thin layer characteristics when applied to silica gel plates developed in either chloroform-methanol (15:1) or heptane-ethyl acetatetriethylamine and infra red spectrum to the compound of Example 1.

EXAMPLE 9

6-Nitro-3,4-dihydro-2-methyl-trans-4-(2-oxo-1-pyrrolidinyl)-2H-benzo[b]pyran-3-ol (E9)

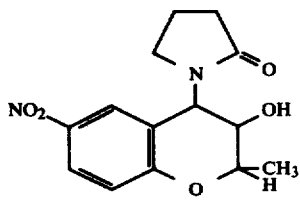
(E9)

The crude ester (0.27 g) of Description 7 was heated under reflux in an atomosphere of nitrogen for 72 hours. Evaporation of solvent and trituration with ethanol and recrystallisation from ethyl acetate gave 6-nitro-3,4-dihydro-2-methyl-trans-4-(2-oxo-1-pyrrolidinyl)-2H-benzo[b]pyran-3-ol as a pale yellow solid (104 mg) of m.p. 238°-242°.

IR (KBr disc) 1650 cm$^{-1}$;

NMR (DMSOd$_6$): δ1.47 (3H, d, J=7 Hz) 1.80-2.23 (2H, m) 2.23-4.00 (5H, series of m) 4.25 (1H, q, J=10, 7 Hz) 5.14 (1H, d, J=10 Hz) 7.02 (1H, d, J=9 Hz) 7.68 (1H, narrow m) 8.06 (1H, q, J=3 Hz).

EXAMPLE 10

7-Nitro-3,4-dihydro-2,2-dimethyl-trans-4-(2-oxo-1-pyrrolidinyl)-2H-benzo[b]pyran-3-ol (E10)

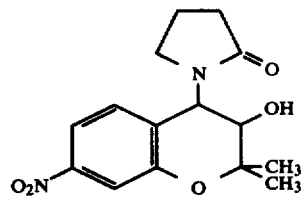
(E10)

The gum of Description 8 was heated under reflux in xylene (30 ml) under nitrogen for 3 days. Evaporation of solvent gave a complex mixture which was purified on a chromatotron (conditions as in Description 8) to give 7-nitro-3,4-dihydro-2,2-dimethyl-trans-4-(2-oxo-1-pyrrolidinyl)-2H-benzo[b]pyran-3-ol (0.04 g) after recrystallisation from ethyl acetate m.p. 211°-211.5° C.

NMR (CDCl$_3$): δ1.30 (3H, s) 1.55 (3H, s) 1.80-3.60 (6H, series of m) 3.80 (1H, d, J=10 Hz) 5.30 (1H, d, J=10 Hz) 7.00-7.85 (3H, m).

EXAMPLE 11

6-Cyano-3,4-dihydro-2,2-dimethyl-trans-4-(2-oxo-1-pyrrolidinyl)-2H-benzo[b]pyran-3-yl acetate (E11)

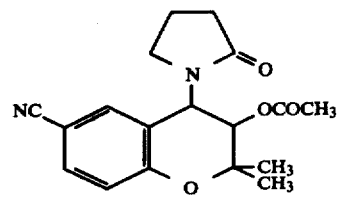
(E11)

6-Cyano-3,4-dihydro-2,2-dimethyl-trans-4-(2-oxo-1-pyrrolidinyl)-2H-benzo[b]pyran-3-ol (0.5 g), acetic anhydride (10 ml) and pyridine (0.2 ml) were refluxed for 24 hours. After cooling the reaction mixture was poured onto ice and extracted with ethyl acetate. The organic layer was washed several times with water, then with NaHCO$_3$ solution and brine before drying over magnesium sulphate. Filtration and evaporation and chromatography of the resulting gum using a chromatotron (2 mm silica gel HF$_{254}$; elution with ethyl acetate), gave a solid (0.35 g) which was recrystallised from ethyl acetate-pentane m.p. 152°-153°, as the title compound.

IR (KBr disc) 2225, 1745, 1695 cm$^{-1}$;

NMR (CDCl$_3$): δ1.35 (3H, s) 1.42 (3H, s) 2.10 (3H, s) overlapped by 1.80-3.40 (6H, m) 5.08 (1H, d, J=10 Hz) 5.45 (1H, d, J=10 Hz) 6.85 (1H, d, J=8 Hz) 7.22 (1H, d, J=2 Hz) 7.40 (1H, q, J=8, 2 Hz).

EXAMPLE 12

6Chloro-3,4-dihydro-2,2-dimethyl-trans-4-(2-oxo-1-pyrrolidinyl)-2H-benzo[b]pyran-3-ol (E12)

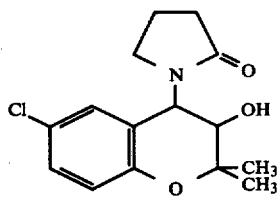
(E12)

2-Pyrrolidone (4.5 g) and sodium hydride (1.59 g) were added to the material of Description 10, and the mixture stirred for 20 hours. Cautions addition of water and filtration of the resulting solid, followed by two crystallisations from ethyl acetate gave the title compound, m.p. 202°-203°.

EXAMPLE 13

6-Acetyl-3,4-dihydro-2,2-dimethyl-trans-4-(2-oxo-1-pyrrolidinyl)-2H-benzo[b]pyran-3-ol (E13)

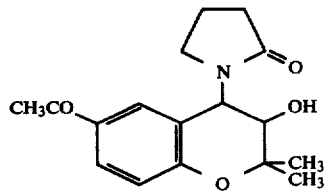
(E13)

6-Acetyl-3,4-dihydro-2,2-dimethyl-3,4-epoxy-2H-benzo[b]pyran (0.33 g, prepared as described in Example 1 of U.K. Pat. No. 1,511,187), and 2-pyrrolidone (0.15 g), were stirred in dimethylsulphoxide (25 ml) under nitrogen at room temperature. Sodium hydride (0.5 g, 80%) was added during 2 mins and the reaction stirred for a further 22 hours. Addition of water, extraction with ethyl acetate, drying of the organic layer with magnesium sulphate, filtration, evaporation and recrystallisation from ethyl acetate gave the title compound (0.04 g) of m.p. 218°-219°.

NMR (CDCl$_3$: δ1.32 (3H, s) 1.55 (3H, s) 1.85-2.25 (2H, m) 2.55 (3H, s) overlapped by 2.45-2.75 (2H, m) 2.80-3.45 (3H, m) 3.75 (1H, d, J=10 Hz) 5.36 (1H, d, J=10 Hz) 6.96 (1H, d, J=8 Hz) 7.63 (1H, narrow m) 7.83 (1H, q, J=8, 2 Hz).

EXAMPLE 14

6-Acetyl-3,4-dihydro-2,2-dimethyl-trans-4-(2-oxo-1-piperidinyl)-2H-benzo[b]pyran-3-ol (E14)

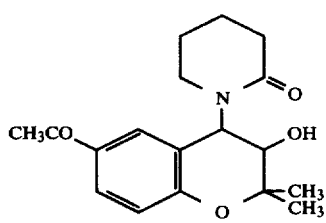

In a similar manner to that described in Example 13 employing 2-piperidone in place of 2-pyrrolidone, the title compound was prepared.

NMR (CDCl$_3$): δ1.29 (3H, s) 1.53 (3H, s) 1.65–2.20 (4H, m) 2.53 (3H, s) overlapped by 2.40–2.75 (2H, m) 2.85–3.20 (2H, m) 3.78 (1H, d, J=10 Hz) overlapped by 3.50–4.00 (1H, m) 5.94 (1H, d, J=10 Hz) 6.88 (1H, d, J=8 Hz) 7.66 (1H, narrow m) 7.80 (1H, q, J=8, 2 Hz).

PHARMACOLOGICAL DATA

Systolic blood pressures were recorded by a modification of the tail cuff method described by I M Claxton, M G Palfreyman, R H Poyser, R L Whiting, European Journal of Pharmacology, 37, 179 (1976). W+W BP recorder, model 8005 was used to display pulses. Prior to all measurements rats were placed in a heated environment (33.5°±0.5° C.) before transfer to a restraining cage. Each determination of blood pressure was the mean of at least 6 readings. Spontaneously hypertensive rats (ages 12–18 weeks) with systolic blood pressures 170 mmHg were considered hypertensive.

| Compound of Example 1 | Time Post Dose Hours | % Change in Systolic Blood Pressure | % Change in Heart Rate |
|---|---|---|---|
| 6 rats | 1 | −47 ± 1 | −2 ± 2 |
| Dose 1 mg/kg | | | |
| po | 2 | −35 ± 4 | −5 ± 3 |
| Initial Blood | 4* | −36 ± 4 | −5 ± 2 |
| Pressure | 6* | −34 ± 3 | −8 ± 2 |
| 211 ± 5 mmHg | | | |
| Initial Heart | 24 | +3 ± 2 | −9 ± 2 |
| Rate | | | |
| 497 ± 3 | | | |
| beats/min | | | |

*At 4 and 6 hours one rat had no measurable pulse.

Compounds of the other examples were also tested and were found also to be active.

TOXICITY

No toxic effects were observed in the above test.
What we claim is:

1. A compound of formula (I):

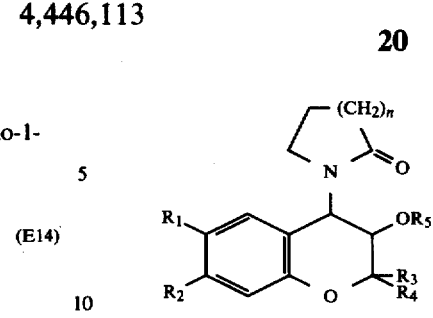

wherein:
one of R$_1$ and R$_2$ is hydrogen and the other is selected from the class of alkylcarbonyl, alkoxycarbonyl, alkylcarbonyloxy, alkylhydroxymethyl, nitro, cyano, chloro, trifluoromethyl, alkylsulphinyl, alkylsulphonyl, alkoxysulphinyl, alkoxysulphonyl, alkylcarbonylamino, alkoxycarbonylamino, or aminosulphinyl, aminosulphonyl or aminocarbonyl, the amino moiety being optionally substituted by one or two alkyl groups, or alkylsulphinylamino, alkylsulphonylamino, alkoxysulphinylamino or alkoxysulphonylamino, or ethylenyl terminally substituted by alkylcarbonyl, nitro or cyano or —C(alkyl)NOH or —C(alkyl)NNH$_2$, the alkyl groups or alkyl moieties of alkyl-containing groups having from 1 to 6 carbon atoms;
one of R$_3$ and R$_4$ is hydrogen or alkyl having from 1 to 4 carbon atoms and the other is alkyl having from 1 to 4 carbon atoms, or R$_3$ and R$_4$ together with the carbon atom to which they are attached are spiroalkyl having from 3 to 6 carbon atoms;
R$_5$ is hydrogen, alkyl having from 1 to 3 carbon atoms or carboxylic acyl having from 1 to 8 carbon atoms; and
n is 1 or 2; the lactam group being trans to the OR$_5$ group.

2. A compound according to claim 1, wherein one of R$_1$ and R$_2$ is hydrogen and the other is selected from the class of alkylcarbonyl, alkoxycarbonyl, alkylcarbonyloxy, alkylhydroxymethyl, nitro or cyano.

3. A compound according to claim 1, wherein the alkyl groups or alkyl moieties of alkyl-containing groups, in respect of the other of R$_1$ and R$_2$, are methyl or ethyl.

4. A compound according to claim 1, wherein R$_3$ and R$_4$ are both alkyl having from 1 to 4 carbon atoms.

5. A compound according to claim 1, wherein R$_5$ is hydrogen.

6. A compound of formula (II):

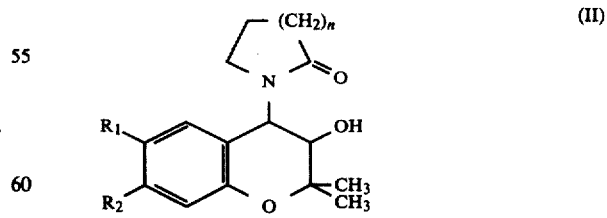

wherein one of R$_1$ and R$_2$ is hydrogen and the other is selected from the class of alkylcarbonyl, alkoxycarbonyl, alkylcarbonyloxy, alkylhydroxymethyl, nitro or cyano, the alkyl groups or alkyl moieties of alkyl containing groups being methyl or ethyl, and n is 1 or 2; the lactam group being trans to the OH group.

7. A compound according to claim 1, wherein one of $R_1$ and $R_2$ is hydrogen and the other is nitro or cyano.

8. A compound according to claim 1 wherein $R_2$ is hydrogen.

9. 6-Cyano-3,4-dihydro-2,2-dimethyl-trans-4-(2-oxo-1-piperidinyl)-2H-benzo[b]pyran-3-ol; 7-nitro-3,4-dihydro-2,2-dimethyl-trans-4-(2-oxo-1-pyrrolidinyl)-2H-benzo[b]pyran-3-ol; 6-cyano-3,4-dihydro-2,2-dimethyl-trans-4-(2-oxo-1-pyrrolidinyl)-2H-benzo[b]-pyran-3-yl acetate; 6-nitro-3,4-dihydro-2-methyl-trans-4-(2-oxo-1-pyrrolidinyl-2H-benzo[b]pyran-3-ol; 6-carbomethoxy-3,4-dihydro-2,2-dimethyl-trans-4-(2-oxo-1-pyrrolidinyl)-2H-benzo[b]pyran-3-ol; 6-carbomethoxy-3,4-dihydro-2,2-dimethyl-trans-4-(2-oxo-1-piperidinyl)-2H-benzo[b]pyran-3-ol; 6-chloro-3,4-dihydro-2,2-dimethyl-trans-4-(2-oxo-1-pyrrolidinyl)-2H-benzo[b]-pyran-3-ol; 6-acetyl-3,4-dihydro-2,2-dimethyl-trans-4-(2-oxo-1-pyrrolidinyl)-2H-benzo[b]pyran-3-ol; and 6-acetyl-3,4-dihydro-2,2-dimethyl-trans-4-(2-oxo-1-piperidinyl)-2H-benzo[b]pyran-3-ol.

10. 6-Cyano-3,4-dihydro-2,2-dimethyl-trans-4-(2-oxo-1-pyrrolidinyl)-2H-benzo[b]-pyran-3-ol.

11. A compound according to claim 1 wherein it is in a substantially pure form.

12. A pharmaceutical composition for treatment of hypertension in mammals, which comprises an antihypertensive effective amount of a compound of formula (I) according to claim 1, and a pharmaceutically acceptable carrier.

13. A method of treatment of hypertension in mammals, which comprises administering an anti-hypertensive effective amount of a compound of formuls (I) according to claim 1 to a mammal in need thereof.

14. The compound of claim 10, in the form of a solid.

15. The compound of claim 14, in the form of a crystalline solid.

16. The compound of claim 14, having a melting point from 226° to 231° C.

17. The compound of claim 16, having a melting point from 230° to 231° C.

18. The compound of claim 10 in pharmaceutically acceptable form.

19. A compound according to claim 8, wherein $R_1$ is cyano and $R_3$ and $R_4$ are both methyl.

20. A compound according to claim 1, wherein one of $R_1$ and $R_2$ is hydrogen, and the other is cyano, nitro, chloro, alkoxycarbonyl, alkylcarbonyloxy or alkylhydroxymethyl.

21. A compound of formula (XIV):

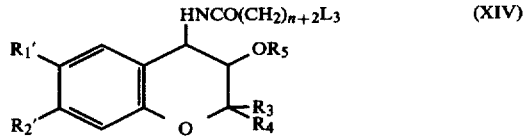

wherein:
one of $R_1$ and $R_2$ is hydrogen and the other is selected from the class of alkylcarbonyl, alkoxycarbonyl, alkylcarbonyloxy, alkylhydroxymethyl, nitro, cyano, chloro, trifluoromethyl, alkylsulphinyl, alkylsulphonyl, alkoxysulphinyl, alkoxysulphonyl, alkylcarbonylamino, alkoxycarbonylamino, or aminosulphinyl, aminosulphonyl or aminocarbonyl, the amino moiety being optionally substituted by one or two alkyl groups, or alkylsulphinylamino, alkylsulphonylamino, alkoxysulphinylamino or alkoxysulphonylamino, or ethylenyl terminally substituted by alkylcarbonyl, nitro or cyano or —C(alkyl)NOH or —C(alkyl)NNH$_2$, the alkyl groups or alkyl moieties of alkyl-containing groups having from 1 to 6 carbon atoms;
one of $R_3$ and $R_4$ is hydrogen or alkyl having from 1 to 4 carbon atoms and the other is alkyl having from 1 to 4 carbon atoms, or $R_3$ and $R_4$ together with the carbon atom to which they are attached are spiroalkyl having from 3 to 6 carbon atoms;
$R_5$ is hydrogen, alkyl having from 1 to 3 carbon atoms or acyl having from 1 to 8 carbon atoms;
n is 1 or 2; and
$L_3$ is chloro, the substituted amino group being trans to the $OR_5$ group.

22. A compound of formula (III):

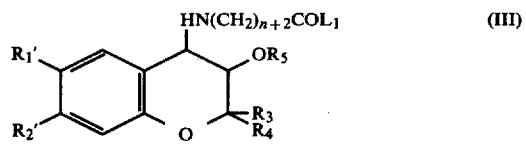

wherein $R_1$ to $R_5$ and n are as defined in claim 1 and $L_1$ is hydroxy or $C_{1-4}$ alkoxy, the substituted amino group being trans to the $OR_5$ group.

23. A compound of formula (IX):

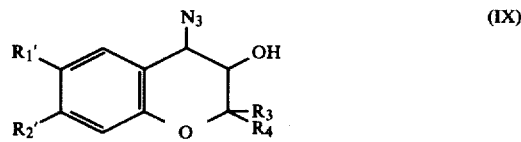

wherein $R_1$ to $R_4$ are as defined in claim 1, the azide group being trans to the hydroxy group.

24. A compound of formula (XI):

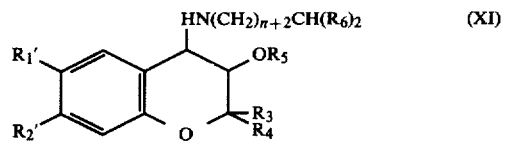

wherein $R_1$ to $R_5$ and n are as defined in claim 1, the substituted amino group being trans to the $OR_5$ group.

25. A compound which is:
6-Cyano-3,4-dihydro-2,2-dimethyl-trans-4-amino-2H-benzo[b]pyran-3-ol,
6-Cyano-3,4-dihydro-2,2-dimethyl-trans-4-(1-keto-4-chlorobutylamino)-2H-benzo[b]pyran-3-ol,
6-Cyano-3,4-dihydro-2,2-dimethyl-trans-4-(4,4-diethoxybutylamino)-2H-benzo[b]pyran-3-ol,
6-Nitro-3,4-dihydro-2-methyl-3,4-epoxy-2H-benzo[b]pyran,
6-Nitro-3,4-dihydro-2-methyl-trans-4-(ethoxycarbonylpropylamino)-2H-benzo[b]pyran-3-ol,
7-Nitro-3,4-dihydro-2,2-dimethyl-trans-4-(3-carbethoxypropylamino)-2H-benzo[b]pyran-3-ol,
6-Chloro-3,4-dihydro-2,2-dimethyl-trans-3-bromo-4-hydroxy-2H-benzo[b]pyran, or
6-Chloro-3,4-dihydro-2,2-dimethyl-3,4-epoxy-2H-benzo[b]pyran.

* * * * *